(12) United States Patent
Ogawa et al.

(10) Patent No.: US 8,853,480 B2
(45) Date of Patent: Oct. 7, 2014

(54) METHOD FOR PRODUCING AROMATIC HYDROCARBON

(75) Inventors: Yuji Ogawa, Kawagoe (JP); Hongtao Ma, Tokyo (JP)

(73) Assignee: Meidensha Corporation, Tokyo (JP)

( * ) Notice: Subject to any disclaimer, the term of this patent is extended or adjusted under 35 U.S.C. 154(b) by 106 days.

(21) Appl. No.: 13/805,756

(22) PCT Filed: Jun. 24, 2011

(86) PCT No.: PCT/JP2011/064523
§ 371 (c)(1),
(2), (4) Date: Dec. 20, 2012

(87) PCT Pub. No.: WO2012/002269
PCT Pub. Date: Jan. 5, 2012

(65) Prior Publication Data
US 2013/0090506 A1    Apr. 11, 2013

(30) Foreign Application Priority Data

Jul. 1, 2010   (JP) ................................ 2010-150878

(51) Int. Cl.
C07C 2/46       (2006.01)
C07C 2/42       (2006.01)
C07C 2/76       (2006.01)

(52) U.S. Cl.
CPC ............... *C07C 2/76* (2013.01); *C07C 2529/48* (2013.01); *Y10S 585/904* (2013.01)
USPC ............................ 585/407; 585/418; 585/904

(58) Field of Classification Search
None
See application file for complete search history.

(56) References Cited

U.S. PATENT DOCUMENTS

| 8,148,590 B2 | 4/2012 | Ichikawa et al. |
| 2010/0137125 A1 | 6/2010 | Ma et al. |
| 2011/0124933 A1 | 5/2011 | Kiesslich et al. |

FOREIGN PATENT DOCUMENTS

| JP | 11-79702 A | 3/1999 |
| JP | 2003-26613 A | 1/2003 |
| JP | 2008-266244 A | 11/2008 |
| JP | 2010-64960 A | 3/2010 |
| WO | WO 2006/011568 A1 | 2/2006 |
| WO | WO 2008/149591 A1 | 12/2008 |
| WO | WO 2009/124960 A1 | 10/2009 |

OTHER PUBLICATIONS

Honda, K. et al., "Methane dehydroaromatization over Mo/HZSM-5 in periodic $CH_4$—$H_2$ switching operation mode", *Catalysis Communications*, vol. 4, (2003), pp. 21-26.

Solymosi, F. et al., "Aromatization of Methane over Supported and Unsupported Mo-Based Catalysts", *Journal of Catalysis*, vol. 165, (1997), pp. 150-161.

*Primary Examiner* — Thuan D Dang
(74) *Attorney, Agent, or Firm* — Foley & Lardner LLP

(57) ABSTRACT

When producing an aromatic hydrocarbon by a contact reaction of a lower hydrocarbon with a catalyst, the aromatic hydrocarbon is produced stably for a long time while maintaining a high aromatic hydrocarbon yield. In a process for producing an aromatic hydrocarbon by being equipped with a reaction step for obtaining the aromatic hydrocarbon by a contact reaction of a lower hydrocarbon with a catalyst and a regeneration step for regenerating the catalyst used in this reaction step, and by repeating the reaction step and the regeneration step, yield of the aromatic hydrocarbon is calculated at constant intervals of time. A yield as the standard is set up from this calculated yield. Based on the change of yield relative to this standard, the regeneration time of the regeneration step is prolonged. A threshold value is set up in the change of yield. In case that the change of yield of the aromatic hydrocarbon has been lower than the threshold value in the reaction step, the regeneration time of the regeneration step is prolonged.

5 Claims, 4 Drawing Sheets

▲ YIELD CHANGE RATE

× BENZENE YIELD CHANGE (a)

BENZENE YIELD (b)

CO₂   CH₄   H₂

METHOD FOR PRODUCING AROMATIC HYDROCARBON

TECHNICAL FIELD

The present invention relates to a high-degree use of natural gas, biogas and methane hydrate, in which methane is a main component. In particular, it relates to a catalytic chemical conversion technique for efficiently producing aromatic hydrocarbons, in which benzene and naphthalenes, which are raw materials of chemical products such as plastics, are main components, and a high-purity hydrogen gas, from lower hydrocarbons such as methane, ethane, propane, etc.

BACKGROUND TECHNIQUE

Natural gas, biogas, and methane hydrate are regarded as the most effective energy resources as global warming measures, and an interest in its use technique is increasing. Methane resource making use of its clean property attracts an attention as the next generation new organic resource and as a hydrogen resource for fuel cells.

As a process for producing hydrogen and aromatic hydrocarbons, such as benzene, from methane, one is known in which methane is reacted in the presence of a catalyst, such as Non-patent Publication 1. As the catalyst upon this, molybdenum supported on ZSM-5 is said to be effective.

However, even in the case of using these catalysts, there are problems that carbon is deposited in large amounts and that conversion of methane is low.

In order to improve the above-mentioned conventional technique, a lower hydrocarbon as the raw material gas (reaction gas) of the aromatic hydrocarbon and a hydrogen-containing gas or hydrogen gas as a gas (regeneration gas) for maintaining the catalytic activity or regenerating the catalytic activity are switched periodically and alternately to make contact reactions with the catalyst (e.g., Patent Publication 1). In this way, the catalytic contact reactions are conducted by alternating the raw material gas and the catalyst regeneration gas to maintain the catalytic reaction while suppressing the deterioration over time of the catalyst.

PRIOR ART PUBLICATIONS

Patent Publications

Patent Publication 1: Japanese Patent Application Publication 2003-26613
Patent Publication 2: Japanese Patent Application Publication Heisei 11-79702

Non-Patent Publications

Non-patent Publication 1: JOURNAL OF CATALYSIS, 1997, Volume 165, p. 150-161

SUMMARY OF THE INVENTION

It is possible to continuously conduct an aromatic hydrocarbon production reaction, while maintaining the catalyst activity, by conducting the catalytic contact reactions by periodically and alternately switching the reaction gas and the regeneration gas, as mentioned above.

In the aromatic hydrocarbon production process described in Patent Publication 1, the catalytic activity is maintained for a long time by previously adding several percent of hydrogen into the reaction gas in order to prevent coking, which is difficult to remove, from accumulating on the catalyst during the catalytic reaction.

$$6CH_4 \rightarrow C_6H_6 + 9H_2 \tag{1}$$

The reaction for producing an aromatic hydrocarbon and hydrogen from a lower hydrocarbon is an equilibrium reaction shown in the formula (1). Therefore, in the case of suppressing coking by adding hydrogen, the benzene formation reaction is suppressed by equilibrium shift. On the other hand, in the case of not adding hydrogen into the reaction gas, yield of the aromatic hydrocarbon is improved, but the formation of coking also becomes vigorous so that the catalyst is deteriorated in a short time.

As the degree of deterioration of the catalyst progresses, the amount of coking to be removed by the catalyst regeneration reaction increases more for that. Therefore, the time required for the catalyst regeneration reaction is prolonged.

Thus, in the aromatic hydrocarbon production process, when an aromatic hydrocarbon is produced by conducting a contact reaction of a lower hydrocarbon with the catalyst, it is requested to stably produce the aromatic hydrocarbon by controlling the balance between the catalytic reaction time and the catalyst regeneration reaction time.

In a process for producing an aromatic hydrocarbon by repeating a reaction step to obtain an aromatic hydrocarbon by conducting a contact reaction of a lower hydrocarbon with the catalyst and a regeneration step to regenerate the catalyst used in the reaction step, the aromatic hydrocarbon production process of the present invention for solving the above task is characterized by that yield of the aromatic hydrocarbon formed in the reaction step is calculated twice or more during the reaction step, that, of these calculated yields, one yield is set as the standard, and that the regeneration time of the regeneration step is changed on the basis of the change of the calculated yield relative to this standard.

Furthermore, the aromatic hydrocarbon production process of the present invention is characterized by that, in the aromatic hydrocarbon production process, a threshold value is set up in the change of the yield, and that the regeneration time of the regeneration step is prolonged when the change of the yield is lower than the threshold value.

Furthermore, the aromatic hydrocarbon production process of the present invention is characterized by that, in the aromatic hydrocarbon production process, when the change of the yield is consecutively lower than the threshold value, the regeneration time of the regeneration step is prolonged.

Furthermore, the aromatic hydrocarbon production process of the present invention is characterized by that, in the aromatic hydrocarbon production process, the regeneration time of the regeneration step is prolonged on the basis of the change of the yield per unit time.

Furthermore, the aromatic hydrocarbon production process of the present invention is characterized by that, in the aromatic hydrocarbon production process, a threshold value is set up in the change per unit time, and that the regeneration time of the regeneration step is prolonged when the change per unit time is lower than the threshold value.

MODE FOR IMPLEMENTING THE INVENTION

Figure 1:
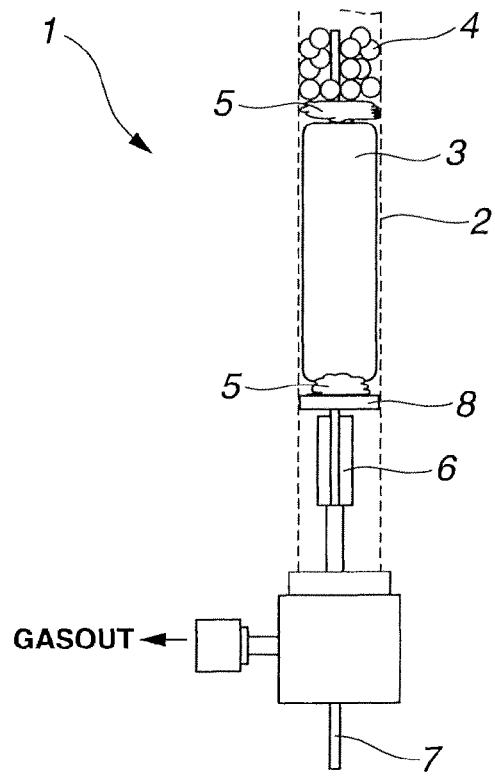
FIG. 1 is a schematic sectional view of a fixed bed, flow type reaction apparatus used in the aromatic compound production process according to an embodiment of the present invention.

The present invention is an invention relating to a process for producing aromatic hydrocarbons, which contains benzene and naphthalenes as main components, and a high-purity hydrogen gas by conducting a contact reaction of a lower hydrocarbon against a catalyst for making aromatic compounds from a lower hydrocarbon (in the following, abbreviated as "catalyst"). It produces aromatic hydrocarbons by alternately conducting a step (reaction step) of conducting the catalytic reaction to produce aromatic hydrocarbons and a step (regeneration step) of conducting the catalyst regeneration reaction to regenerate the catalyst used in this catalytic reaction. In this reaction step, yield of the aromatic hydrocarbons (e.g., benzene) formed by the catalytic reaction is calculated. It is characterized by that one yield is set up as the standard out of these calculated yields and that the catalytic reaction time or the catalyst regeneration time is controlled on the basis of the change of the calculated yield relative to this standard. By indirectly understanding the condition of coking on the basis of the product yield change during the catalytic reaction in this way, it is possible to conduct a feedback control on the reaction condition in accordance with the degree of coking. Therefore, even if a process of suppressing the catalytic reaction, such as previously adding hydrogen, is not used, it is possible to conduct the catalytic reaction continuously while maintaining yield of aromatic hydrocarbons at high levels.

As the catalyst used in the aromatic hydrocarbon production process according to an embodiment of the present invention, it is possible to mention, for example, a form in which a catalyst metal is supported on a metallosilicate.

As the metallosilicate having a catalyst metal supported thereon, for example, in the case of aluminosilicate, it is possible to cite molecular sieve 5A, faujasite (NaY and NaX), ZSM-5 and MCM-22, which are porous materials formed of silica and alumina. Furthermore, it can be exemplified by zeolite supports, which are porous materials having phosphoric acid as a main component and are characterized by having 6-13 angstrom micropores and channels, such as ALPO-5 and VPI-5. Furthermore, it can be exemplified by meso-porous supports, which contain silica as a main component and partly alumina as a component and are characterized by cylindrical micropores (channels) of meso-micropores (10-1000 angstroms), such as FSM-16 and MCM-41. Furthermore, besides the aluminosilicate, it is also possible to use a metallosilicate formed of silica and titania, etc. as the catalyst.

Furthermore, it is desirable that a metallosilicate used in the present invention has a surface area of 200-1000 $m^2$/g and that its micro- and meso-pores are within a range of 5-100 angstroms. Furthermore, in case that the metallosilicate is, for example, aluminosilicate, it is possible to use one in which the ratio of silica content to alumina content (silica/alumina) is 1-8000, similar to porous materials that are generally available. It is, however, more preferable to make silica/alumina within a range of 10-100 in order to conduct an aromatization reaction of a lower hydrocarbon of the present invention with a practical lower hydrocarbon conversion and a selectivity to an aromatic hydrocarbon.

As the metallosilicate, it is general to use a proton-exchanged type (H type). Furthermore, the proton may be partly exchanged for at least one cation selected from alkali metals such as Na, K and Li, alkali-earth elements such as Mg, Ca and Sr, and transition metal elements such as Fe, Co, Ni, Zn, Ru, Pd, Pt, Zr and Ti. Furthermore, the metallosilicate may contain a suitable amount of Ti, Zr, Hf, Cr, Mo, W, Th, Cu, Ag, etc.

Then, it is preferable to use molybdenum as a catalyst metal of the present invention, but it is also possible to use rhenium, tungsten, iron, and cobalt. A combination of these catalyst metals may be supported on the metallosilicate. Furthermore, besides these catalyst metals, at least one element selected from alkali-earth elements, such as Mg, or transition metal elements, such as Ni, Zn, Ru, Pd, Pt, Zr and Ti, may be supported on the metallosilicate.

In the case of supporting the catalyst metal (a precursor containing the same) on a metallosilicate, it is conducted to have a weight ratio of the catalyst metal to the support of a range of 0.001-50%, preferably 0.01-40%. Furthermore, as a method of supporting on the metallosilicate, there is a method in which a supporting is conducted on a metallosilicate support by impregnation or an ion exchange method from a catalyst metal precursor aqueous solution or solution of an organic solvent such as alcohol, and then a heating treatment is conducted under an atmosphere of an inert gas or oxygen gas. For example, as examples of a precursor containing molybdenum as one of the catalyst metals, it is possible to cite halides such as chlorides and bromides, mineral acid salts such as nitrates, sulfates and phosphates, carboxylates such as carbonates, acetates and oxalates, etc., besides ammonium paramolybdate, ammonium phosphomolybdate, 12-series molybdic acids.

Herein, a process of supporting the catalyst metal on a metallosilicate is explained by showing as an example a case of using molybdenum as the catalyst metal. Firstly, an impregnation supporting of an ammonium molybdate aqueous solution is conducted on a metallosilicate support, and the supported substance is dried under reduced pressure to remove the solvent, and then a heating treatment is conducted at a temperature of 250-800° C. (preferably 350-600° C.) in a nitrogen-containing oxygen stream or a pure oxygen stream. With this, it is possible to produce a metallosilicate catalyst supporting molybdenum.

The form of the metallosilicate catalyst supporting a catalyst metal is not particularly limited. It suffices to use one having an arbitrary shape such as powdery and granular. The metallosilicate catalyst supporting thereon a catalyst metal may be used by shaping into pellets or an extrusion after adding a binder such as silica, alumina and clay.

Furthermore, in the present invention, lower hydrocarbons mean methane and $C_{2-6}$ saturated and unsaturated hydrocarbons. These $C_{2-6}$ saturated and unsaturated hydrocarbons can be exemplified by ethane, ethylene, propane, propylene, n-butane, isobutane, n-butene, and isobutane, etc.

The reactor used in the method for producing an aromatic hydrocarbon of the present invention is exemplified by a fixed bed reactor or flow bed reactor, etc.

The amount of raw material input is 150-70000 [ml/g-MFI/h], preferably 500-30000 [ml/g-MFI/h], more preferably 1400-14000 [ml/g-MFI/h], in terms of weight hourly space velocity (WHSV) relative to the amount of the catalyst.

The reaction temperature is 600° C. to 900° C., preferably 700° C. to 850° C., more preferably 750° C. to 830° C. The reaction pressure is 0.1 to 0.9 MPa, preferably 0.1 to 0.5 MPa.

In the following, a more detailed explanation is conducted by showing an example of the aromatic hydrocarbon production process according to the present invention.

EXAMPLE

A catalyst was prepared by the following preparation process using H-type ZSM-5 zeolite ($SiO_2/Al_2O_3$=25-70) as a metallosilicate support.

(Production of Catalyst)

In the present example, a catalyst modified by a silane coupling agent was prepared. The zeolite support was immersed for a predetermined time in an ethanol in which a silane compound had been dissolved. This was dried, followed by a sintering at 550° C. for 6 hours, thereby obtaining a zeolite subjected to a silane treatment by the silane compound.

Then, an aqueous solution for impregnation was prepared to have a predetermined molar ratio after supporting thereon ammonium molybdate and zinc nitrate (zinc acetate is also acceptable). In the present example, the aqueous solution for impregnation was prepared by adjusting the amount of supporting of the metal (e.g., Mo) to be supported by impregnation to 6 wt % and by using another metal (e.g., Zn) together with Mo for impregnation to have a molar ratio of Zn:Mo=0.3:1. The amount of supporting of the metal to be supported by impregnation and the molar ratio of the metal to be supported by impregnation and the metal used together therewith for impregnation are not limited to those of this example. It suffices to suitably select the amount of the metal supported and the molar ratio for obtaining the target catalytic activity.

The silane-treated zeolite was immersed in this aqueous solution to impregnate the zeolite support with molybdenum and zinc. The support after the impregnation was dried while controlling humidity and temperature. Then, the dried product was sintered in the air at 550° C. for 5 hours to obtain a silane-modified, zinc/molybdenum-supported ZSM-5 (Zn (1.23 wt %)/Mo (6 wt %)/HZSM-5).

(Composition)

Composition of only inorganic components: ZSM-5 (82.5%), clay (12.5%) and glass fibers (5%).

Composition in total: inorganic components (76.5%), an organic binder (17.3%) and water (24.3%).

(Molding Method)

The inorganic components, the organic binder and water of the above composition were combined together, followed by mixing and kneading using a kneader, etc. This mixture was molded into a rod shape (φ2.4 mm×L 5 mm) by using a vacuum extruder. The extrusion pressure upon this molding was 2 to 8 MPa.

(Drying and Sintering)

The drying was conducted by a drying at 70° C. for 12 hours for removing water added upon the molding and then a drying at 90° C. for about 36 hours. The sintering temperature was set to be in a range of 550 to 800° C. This is because there may occur a lowering of strength of the support if it is lower than 550° C. and because there may occur a lowering of its characteristics if it is higher than 800° C.

(Measurement Conditions)

The catalyst subjected to the above metal supporting treatment was put into a reaction tube 2 (inner diameter 18 mm) made by an Inconel 800H, gas-contact portion calorizing treatment of a fixed bed flow-type reaction apparatus 1 shown in FIG. 1. A test for producing aromatic hydrocarbons from a lower hydrocarbon was conducted under the reaction conditions shown in Table 1. Carbon dioxide added to the reaction gas has an advantageous effect of stabilizing the reaction for producing aromatic compounds from a lower hydrocarbon.

TABLE 1

| REACTION CONDITIONS OF ACTIVITY TEST | |
|---|---|
| | Reaction conditions |
| Amount of catalyst loaded | 10 g |
| Zeolite content in molded body | 82.50% |
| Supply gas | 100 methane ($CH_4$) + 3 carbonic acid gas ($CO_2$) |
| Reaction SV | 3000 ml/g-MFI/h ($CH_4$ gas flow base) |
| Reaction temperature | 820° C. |
| Reaction pressure | 0.15 MPa |

A pretreatment of the catalyst was conducted, prior to conducting a contact reaction of the lower hydrocarbon with the catalyst. In the pretreatment of the catalyst, the catalyst was subjected to a temperature rising until 550° C. under flow of the air, followed by maintenance for 2 hours, switching to a pretreatment gas of 20% methane and 80% hydrogen, a temperature rising until 700° C., and maintenance for 3 hours. Then, it was switched to the reaction gas, followed by a temperature rising until a predetermined temperature (820° C.), and then evaluating the catalyst. In the analysis of the components in the gas after the reaction, hydrogen, argon and methane were analyzed by TCD-GC, and aromatic hydrocarbons such as benzene, toluene, xylene, and naphthalene were analyzed by FID-GC.

The catalyst was evaluated by yield of benzene relative to the lower hydrocarbon made to flow. Benzene yield was defined as shown in the following formula (2).

$$\text{Benzene yield (\%)} = \{(\text{mol number of benzene formed in terms of carbon})/(\text{mol number of methane used for the methane reforming reaction})\} \times 100 \quad (2).$$

The regeneration of the catalyst used for the catalytic reaction was conducted by changing the supply gas stated in the above Table 1 to hydrogen gas to make a contact reaction between the catalyst and hydrogen. The regeneration gas is not limited to hydrogen, but a reducing gas is acceptable. Furthermore, it is optional to use gases containing these reducing gases.

(1) Changes of Benzene Yield and Yield Change Rate in the Case of Conducting Only the Reaction Step In a process for producing an aromatic hydrocarbon by alternately repeating a reaction step to produce an aromatic hydrocarbon by conducting a contact reaction of a lower hydrocarbon with a catalyst and a regeneration step to regenerate the catalyst used in this reaction step, the catalyst production process according to an embodiment of the present invention is one in which the yield change rate is calculated on the basis of benzene yield, and on the basis of this yield change rate the regeneration time of the catalyst regeneration time is prolonged.

When one of aromatic hydrocarbon yields calculated twice or more in the reaction step is set as the standard, the yield change rate is calculated as the change rate of another yield relative to the yield as this standard. When calculating the yield change rate (or the after-mentioned benzene yield change), it suffices to suitably select an arbitrary yield as the yield of aromatic hydrocarbon set as the standard as long as it is in a range wherein the aromatic hydrocarbon yield improves after switching to the reaction step. In particular, it is advantageous to set the yield, which has been calculated during a period of time from immediately after the start of the reaction to 15 minutes after the start of the reaction, as the standard. Furthermore, it is optional to set the maximum value of aromatic hydrocarbon yield, which has been calculated in the reaction step, as the standard.

For example, in case that the yield, which has firstly been measured after the start of the reaction step, is set as the standard of aromatic hydrocarbon (e.g., benzene) yield, the yield change rate is shown by the formula (3). In the formula (3), t is the elapsed time in the reaction step (the unit may be an arbitrary unit, such as minute, hour, etc.).

Yield change rate=[{(benzene yield after an elapse of time "$t$" in the reaction step)−(benzene yield calculated for the first time after the start of the reaction step)}/(benzene yield calculated for the first time after the start of the reaction step) (3)

The aromatization reaction of the lower hydrocarbon was continuously conducted under the reaction conditions shown in the above Table 1. The benzene yield was calculated at intervals of 1 hour in reaction time of the reaction step. By substituting this benzene yield into the above formula (3), the yield change rate of benzene was calculated. The calculation results of benzene yield and yield change rate are shown in Table 2 and FIG. 2.

TABLE 2

| Reaction time (hr) | Benzene yield (%) | Yield change rate | Benzene yield change (%/h) |
|---|---|---|---|
| 1.00 | 10.70 | | |
| 2.00 | 11.40 | 0.07 | 0.70 |
| 3.00 | 11.10 | 0.04 | 0.20 |
| 4.00 | 10.00 | −0.07 | −0.23 |
| 5.00 | 7.70 | −0.28 | −0.75 |
| 6.00 | 2.30 | −0.79 | −1.68 |
| 7.00 | 0.10 | −0.99 | −1.77 |

Figure 2:
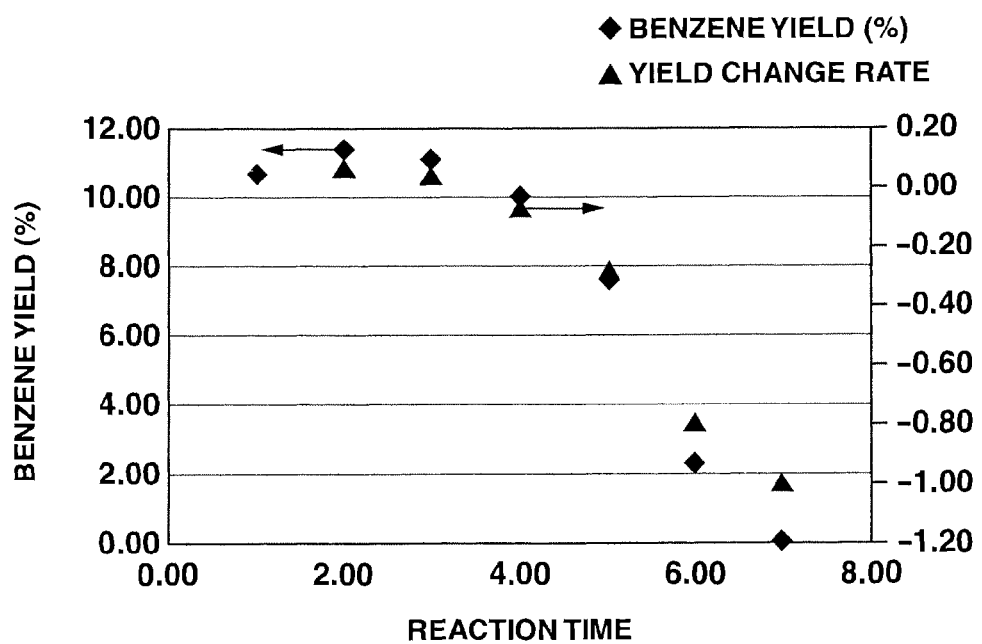
FIG. 2 is a graph showing the changes over time of the benzene yield and the yield change rate in case that the catalytic reaction was conducted continuously.

As clear from FIG. 2, in the case of continuously conducting the reaction step, benzene yield lowers abruptly and finally takes a value close to 0%. It is considered that this is because carbon precipitates on the catalyst in the course of time of the reaction step. Looking at the yield change rate of benzene, a high benzene yield is maintained when the yield change rate of benzene is −0.07 or higher. Therefore, it is possible to repeatedly conduct the reaction step, while maintaining a high benzene yield, by setting the threshold value of the yield change rate at −0.07 or higher and by making a setting to prolong the catalyst regeneration time when the yield change rate takes a value lower than this threshold value.

The change of the yield change rate between 4 hours and 5 hours in the reaction time is 0.2, and the change of the yield change rate between 5 hours and 6 hours in the reaction time is more than 0.4. That is, when the yield change rate of benzene takes a value higher than −0.28, the degree of lowering of the yield change rate is gentle. Therefore, when the value of the threshold value is set at −0.28 or higher, it is possible to suppress lowering of benzene yield and prolong the catalytic reaction time in the entire production steps (the reaction step and the regeneration step).

As mentioned above, in order to conduct the catalytic reaction while prolonging the catalytic reaction time in the entire production steps and maintaining a high benzene yield, it is advantageous to set the threshold value of the yield change rate, which becomes the standard to prolong the regeneration time of the regeneration step, at −0.07 to −0.28.

It is optional to prolong the regeneration time of the regeneration step by using one of the yields of the aromatic hydrocarbon, which are calculated twice or more in the reaction step, as a standard, on the basis of the change of another yield relative to the yield as this standard per unit time (the change of yield), in place of the yield change rate exemplified by the above formula (3).

For example, as shown by the following formula (4), there is calculated the change of benzene yield per unit time on the basis of the yield measured for the first time after the start of the reaction step. In the formula (4), t is the elapsed time in the reaction step (the unit may be an arbitrary unit, such as minute, hour, etc.).

Benzene yield change=[{(benzene yield after an elapse of time "$t$" in the reaction step)−(benzene yield calculated for the first time after the start of the reaction step)}/{$t$−(the elapsed time in the reaction when the benzene yield was calculated for the first time after the reaction step)} (4)

In the above Table 2, the change of benzene yield calculated based on formula (4) is shown. Similar to the yield change rate, when the change of benzene yield is −0.23 or higher, a high benzene yield is maintained. When the change of benzene yield has a value higher than −0.75, the degree of lowering of benzene yield is mild. Therefore, in order to conduct the catalytic reaction with a long catalytic reaction time in the entire production steps while maintaining a high benzene yield, it is advantageous to set the threshold value of the benzene yield change as the standard for prolonging the regeneration time of the regeneration step at −0.23 to −0.75.

Figure 3:
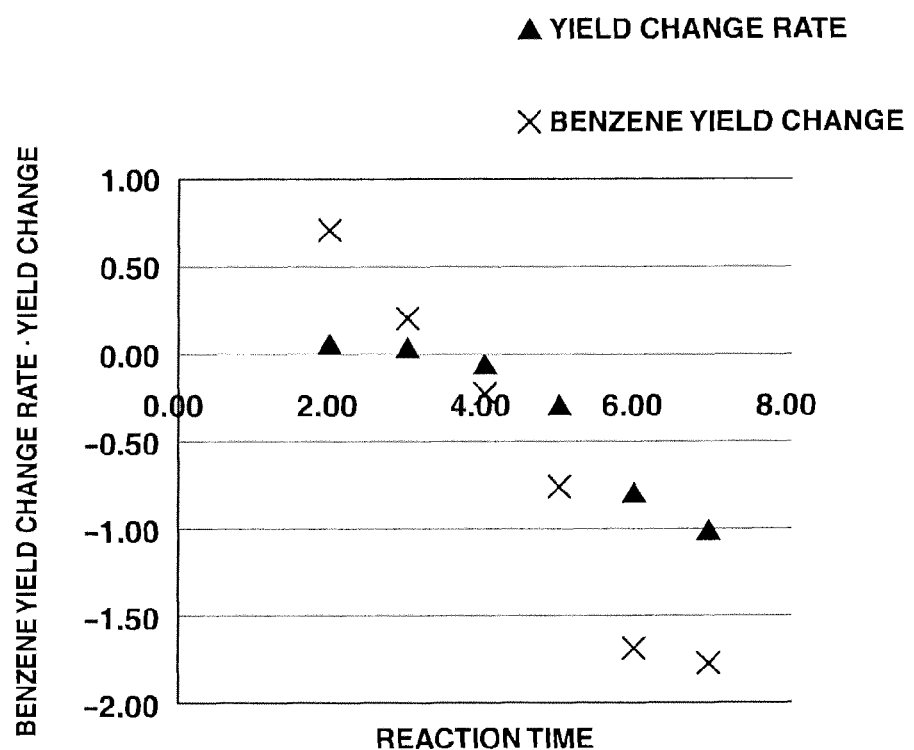
FIG. 3 is a graph showing the benzene yield change rate and the benzene yield change in case that the catalytic reaction was conducted continuously.

As shown in FIG. 3, as compared with the yield change rate, the benzene yield change shows a clear difference between benzene yield changes at respective measurement times. Therefore, it is hardly affected by the effect of measurement errors, and it is possible to more accurately conduct the comparison between the measured value and the threshold value.

Figure 4:
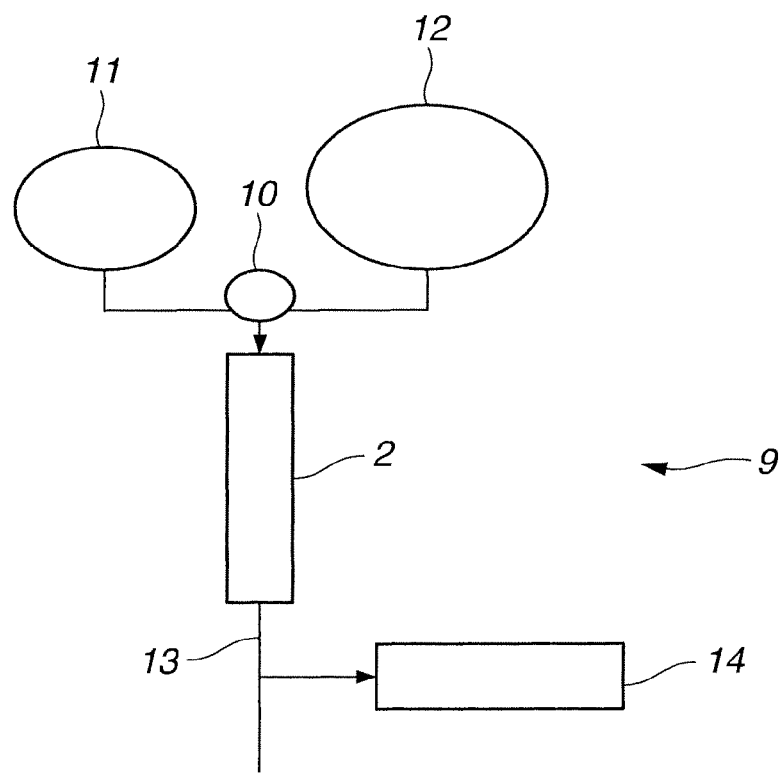
FIG. 4 is a schematic diagram of the aromatic hydrocarbon production apparatus used in the aromatic compound production process according to an embodiment of the present invention.

(2) Variations of the Benzene Yield and Yield Change in the Case of Repeating the Reaction Step and the Regeneration Step As shown in FIG. 4, an aromatic hydrocarbon production apparatus 9 according to an embodiment of the present invention is such that a raw material supply section 11 for supplying the raw material gas and a regeneration gas supply section 12 for supplying a regeneration gas for regenerating the catalyst are connected to a reaction tube 2 of a fixed bed, flow, reaction apparatus 1 through a switching valve 10. Furthermore, a gas exhaust pipe 13 for exhausting a gas (exhaust gas) after subjecting to a contact reaction with the catalyst of the reaction tube 2 is connected to the reaction tube 2, and a detector 14 is connected by branching off from the gas exhaust pipe 13. The detector 14 detects aromatic hydrocarbons, etc. in the exhaust gas by gas chromatography or the like. Based on the detection results at the detector 14, the product (e.g., benzene) yield, the yield change rate and the yield change are calculated at a calculation section not shown in the drawing.

Figure 5:
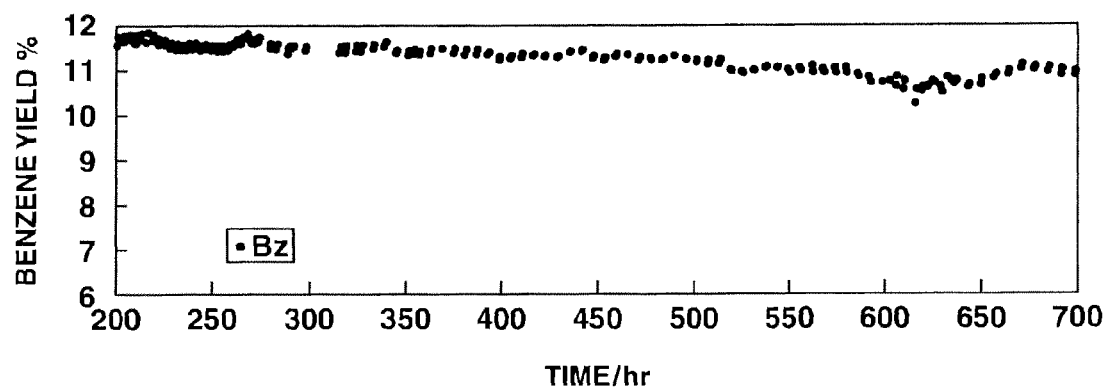
FIG. 5 is a graph showing the change over time of the benzene yield in case that the catalytic reaction and the catalyst regeneration reaction were conducted alternately.

In the present example, the catalytic reaction was conducted for one hour by switching the switching valve 10 and then introducing the raw material gas (methane) into the reaction tube 2 from the raw material gas supply section 11. Then, the regeneration reaction was conducted for 1.5 hours by switching the switching valve 10 and introducing the regeneration gas (hydrogen) into the reaction tube 2 from the regeneration gas supply section 12. Then, the reaction step and the regeneration step were alternately repeated to produce aromatic hydrocarbons by a contact reaction between a lower hydrocarbon and the catalyst. Benzene was detected by the detector 14, and the benzene yield calculated by the formula (2) was measured at constant intervals (intervals of 60 minutes). Then, based on the benzene yield measured and the above formula (4), the benzene yield change was calculated. It is advantageous to conduct the measurement of the benzene yield at intervals of 10 minutes to 60 minutes. The prolongation of the measurement intervals beyond 60 minutes is not preferable, since the deterioration due to coking during the reaction is strong in a reaction with the addition of no hydrogen to the reaction gas. It is advantageous to set the measurement intervals in accordance with the performance of the detector 14 such as a gas chromatograph. The measurement may be conducted in real time. Variation with time of the benzene yield is shown in FIG. 5, and variation with time of the benzene yield change is shown in FIG. 6.

Figure 6:
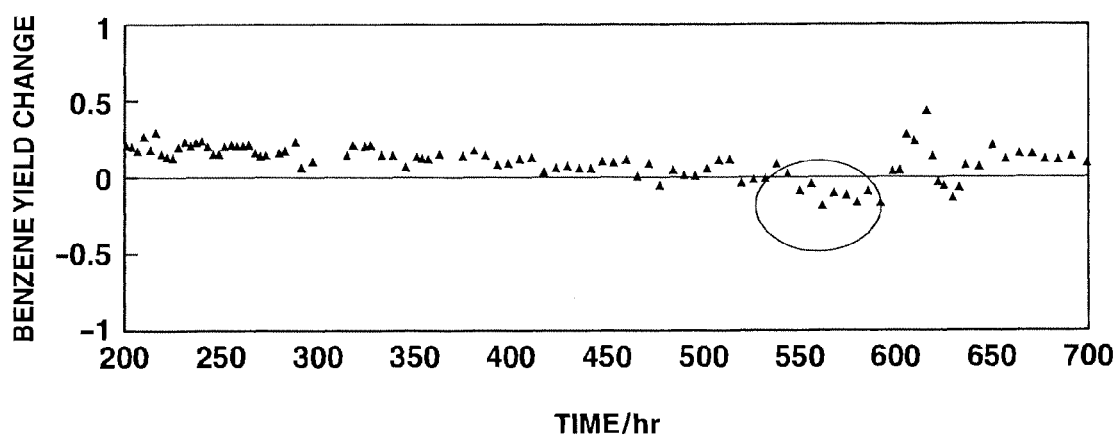
FIG. 6 is a graph showing the change over time of the benzene yield change in case that the catalytic reaction and the catalyst regeneration reaction were conducted alternately.

As shown in FIG. 6, the benzene yield change was in positive values until 500 hours of the aromatic hydrocarbon production reaction. From around 550 hours, the benzene yield change turned to negative values. At this time, a large change is not found in the benzene yield shown in FIG. 5. By repeating the catalytic reaction and the regeneration reaction while the benzene yield change is in negative values, lowering of the benzene yield becomes conspicuous at around 580 hours in the graph shown in FIG. 5. Thus, the setting was changed at 591.5 hours to conduct the catalytic reaction step for 1 hour and the catalyst regeneration step for 2 hours. As a result of this, the benzene yield change turned to positive values (FIG. 6), and the benzene yield also improved (FIG. 5).

Thus, it is possible to previously detect lowering of the benzene yield by the benzene yield change defined in the present invention. It was confirmed by an experiment that lowering of the benzene yield could be previously detected similarly by the yield change rate calculated by the formula (3), too. Therefore, it is understood that the yield change rate and the benzene yield change are effective indicators for determining the switch timing of the reaction step and the regeneration step in the aromatic hydrocarbon production process by repeating the reaction step and the regeneration step. In case that the benzene yield change has consecutively been in negative values several times, it is possible to reduce the effect of the measurement errors by prolonging the regeneration time. The prolongation of the regeneration time may suitably be set depending on how many consecutive times it falls below the threshold value. It is advantageous to set the number of consecutive times at 2 to 5.

Figure 7:
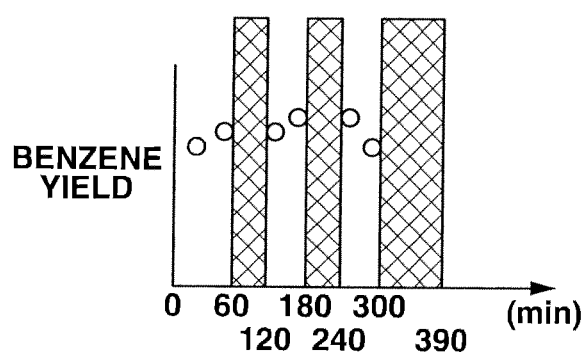
FIG. 7 are diagrams showing outlines of the aromatic hydrocarbon production step by repeating the reaction step and the regeneration step according to the present invention, (a) being a graph showing the calculation results of the yield in the reaction step, and (b) being a graph showing the switching time of the reaction step and the regeneration step.
Figure 7:
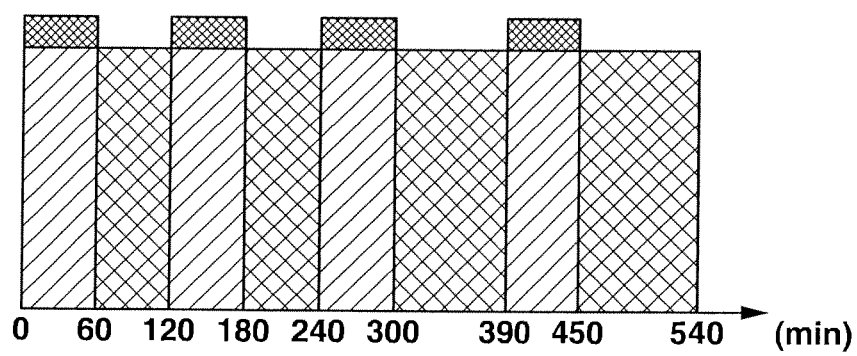

In FIG. 7, there are shown schematic views of the aromatic hydrocarbon production step by repeating the reaction step and the regeneration step according to the present example. In the example shown in FIG. 7, as shown in FIG. 7(*b*), there is shown an example by alternately repeating the reaction step for producing aromatic hydrocarbons by reacting a methane containing carbon dioxide with the catalyst and the regeneration step for regenerating the catalyst activity by bringing hydrogen into contact with the catalyst used in this reaction step, for one hour each.

The benzene yield was measured at intervals of one hour in the reaction step. Based on the above formula (4), the benzene yield change was calculated. In this example, in case that the benzene yield change had become negative, the regeneration time of the regeneration step was prolonged by 0.5 hours (that is, the threshold value was set at 0).

As shown in FIG. 7(*a*), in the reaction step, the benzene yield was calculated at the start of the reaction and at the end of the reaction (it is shown by O in the drawing). In the reaction step from 240 minutes to 300 minutes, the benzene yield after the reaction was lower than the benzene yield at the start of the reaction (that is, the benzene yield change was negative). Therefore, the regeneration step was prolonged. As shown in FIG. 7(*a*), the regeneration step subsequent to the reaction step from 240 minutes to 300 minutes was prolonged for 0.5 hours.

Thus, it is possible to conduct the catalytic reaction, while maintaining a high benzene yield for a long time, by changing the length of the regeneration time based on the benzene yield change. The reaction time of the reaction step and the regeneration time and the extra time of the regeneration step are not limited to the above example, but may suitably be set. For example, if the reaction time of the reaction step is adjusted to a reaction time that the benzene yield change at the end of the reaction step is in a range from 0.2 to 1, it is possible to conduct the reaction step with a high benzene yield. The regeneration time may be adjusted to a time necessary for restoring the catalytic activity to a catalytic activity at the start of the reaction step. It is advantageous to adjust the extra time to prolong the regeneration step to 10% to 30% of the regeneration time in the regeneration step. This is because the catalyst regeneration effect is sufficiently obtained by making the extra time long and because the time occupied by the reaction step in the entire production steps becomes long by making the extra time short, thereby improving the aromatic hydrocarbon production efficiency.

The threshold value of the benzene yield change, which is an indicator to prolong the regeneration time of the regeneration step, is also not limited to negative values, but can suitably be set. In particular, it is advantageous to adjust the threshold value of the benzene yield change calculated by the formula (4) to from −0.23 to −0.75.

As mentioned above, according to the process of the present invention for producing aromatic hydrocarbons and hydrogen by a contact reaction of a lower hydrocarbon with the catalyst, it is possible to detect lowering of benzene yield before the benzene yield lowering phenomena becomes evident. Therefore, it is possible to conduct the aromatic hydrocarbon production reaction for a long time while maintaining a high benzene yield (catalytic activity).

In an apparatus for producing aromatic hydrocarbons by a contact reaction between the catalyst and a lower hydrocarbon, yield of the aromatic hydrocarbon also changes depending on the reaction conditions and the type of the catalyst. Even in the same reaction conditions, yield of the aromatic hydrocarbon changes by repeating the reaction step for conducting the catalytic reaction and the regeneration step for regenerating the catalyst used in this reaction step. By the indicators (the yield change rate and the benzene yield change) according to the present invention, it is possible to previously detect lowering of the benzene yield and judge the catalyst deterioration condition.

As above, in the present invention, a detailed explanation was made only on a specific example described. It is, however, clear to a person skilled in the art that various modifications and revisions are possible within a technological idea of the present invention, and it is natural that such modifications and revisions belong to the scope of the claims.

For example, as an alternative to the yield change rate illustrated in the example, it is optional to use {(the benzene yield after conducting the catalytic reaction for "t" minutes from the start of the catalytic reaction)–(the benzene yield at the start of the catalytic reaction)} as the yield change rate (t is an arbitrary set time). Thus, it is possible to evaluate the degree of lowering of the benzene yield on the basis of the benzene yield at the start of the reaction step by setting the yield change rate.

Furthermore, it is optional to switch from the reaction step to the regeneration step in case that the yield change rate (or the benzene yield change) has fallen below the predetermined threshold value while measuring the yield in real time.

| EXPLANATION OF SIGNS | |
|---|---|
| 1 | a fixed bed, flow type reaction apparatus |
| 2 | a reaction tube |
| 3 | a catalyst |
| 4 | alumina balls |
| 5 | a quartz glass wool |
| 6 | a quartz glass tube |
| 7 | a thermocouple tube |
| 8 | a catch basin |
| 9 | an aromatic hydrocarbon production apparatus |
| 10 | a switching valve |
| 11 | a raw material gas supply section |
| 12 | a regeneration gas supply section |
| 13 | a gas exhaust pipe |
| 14 | a detector |

The invention claimed is:

1. In a process for producing an aromatic hydrocarbon by repeating a reaction step to obtain an aromatic hydrocarbon by conducting a contact reaction of a lower hydrocarbon with a catalyst and a regeneration step to regenerate the catalyst used in the reaction step,
the aromatic hydrocarbon production process being characterized by that yield of the aromatic hydrocarbon formed in the reaction step is calculated twice or more during the reaction step, that, of these calculated yields, one yield is set as a standard, and that the regeneration time of the regeneration step is changed on the basis of the change of the calculated yield relative to this standard.

2. The aromatic hydrocarbon production process as claimed in claim 1, which is characterized by that a threshold value is set up in the change of the yield, and that the regeneration time of the regeneration step is prolonged when the change of the yield is lower than the threshold value.

3. The aromatic hydrocarbon production process as claimed in claim 2, which is characterized by that, when the change of the yield is consecutively lower than the threshold value, the regeneration time of the regeneration step is prolonged.

4. The aromatic hydrocarbon production process as claimed in claim 1, which is characterized by that the regeneration time of the regeneration step is prolonged on the basis of the change of the yield per unit time.

5. The aromatic hydrocarbon production process as claimed in claim 4, which is characterized by that a threshold value is set up in the change per unit time, and that the regeneration time of the regeneration step is prolonged when the change per unit time is lower than the threshold value.

* * * * *